United States Patent [19]

Okamoto et al.

[11] 4,133,880

[45] Jan. 9, 1979

[54] N²-SUBSTITUTED-L-ARGININE DERIVATIVES AND THE PHARMACEUTICALLY ACCEPTABLE ACID ADDITION SALTS THEREOF

[75] Inventors: Shosuke Okamoto, 15-18, Asahigaoka 3-chome, Tarumi-ku, Kobe-shi, Hyogo; Akiko Hijikata, Kobe; Ryoji Kikumoto, Machida; Yoshikuni Tamao, Yokohama; Kazuo Ohkubo, Machida; Tohru Tezuka, Yokohama; Shinji Tonomura, Tokyo, all of Japan

[73] Assignees: Mitsubishi Chemical Industries Ltd., Tokyo; Shosuke Okamoto, Hyogo, both of Japan

[21] Appl. No.: 819,872

[22] Filed: Jul. 28, 1977

Related U.S. Application Data

[60] Division of Ser. No. 703,704, Jul. 8, 1976, Pat. No. 4,069,323, which is a continuation-in-part of Ser. No. 671,436, Mar. 29, 1976, Pat. No. 4,066,758, which is a division of Ser. No. 622,390, Oct. 14, 1975, abandoned.

[30] Foreign Application Priority Data

| Aug. 8, 1975 | [JP] | Japan | 50-96417 |
| Sep. 2, 1975 | [JP] | Japan | 50-106139 |
| Sep. 11, 1975 | [JP] | Japan | 50-110242 |
| Oct. 1, 1975 | [JP] | Japan | 50-118525 |
| Oct. 7, 1975 | [JP] | Japan | 50-121173 |
| Nov. 8, 1974 | [JP] | Japan | 49-128774 |
| Nov. 8, 1974 | [JP] | Japan | 49-128775 |
| Nov. 29, 1974 | [JP] | Japan | 49-136695 |
| Nov. 29, 1974 | [JP] | Japan | 49-136697 |
| Feb. 25, 1975 | [JP] | Japan | 50-023268 |
| Feb. 26, 1975 | [JP] | Japan | 50-023635 |
| Mar. 5, 1975 | [JP] | Japan | 50-026768 |
| Mar. 11, 1975 | [JP] | Japan | 50-029357 |
| Mar. 11, 1975 | [JP] | Japan | 50-029358 |

[51] Int. Cl.² ............... A61K 31/495; A61K 31/505; A61K 31/535; A61K 31/54
[52] U.S. Cl. .................................. 424/244; 544/8; 544/54; 260/239 A; 544/58; 544/63; 260/239 BC; 544/65; 544/66; 260/306.7 R; 544/67; 544/88; 260/307 FA; 544/96; 544/148; 260/308 R; 544/150; 544/151; 260/308 A; 544/153; 544/159; 260/327 R; 544/179; 544/182; 260/333; 544/215; 544/224; 260/335; 544/233; 544/333; 260/338; 544/335; 544/375; 260/340.3; 544/376; 544/377; 260/345.2; 544/391; 548/300; 260/346.71; 548/356; 424/246; 424/248.5; 424/249; 424/250; 424/251; 424/269; 424/270; 424/272; 424/273 R; 424/275; 424/276; 424/277; 424/278; 424/283; 424/285; 544/2; 544/3; 544/5; 544/7
[58] Field of Search ..... 260/239 A, 239 BC, 306.7 R, 260/307 FA, 308 R, 308 A, 327 R, 333, 335, 336, 340.3, 345.2, 346.71; 424/244, 246, 248.5, 249, 250, 251, 269, 270, 272, 273 R, 275, 276, 277, 278, 283, 285; 544/2, 3, 5, 7, 8, 54, 58, 63, 65, 66, 67, 88, 96, 148, 150, 151, 153, 159, 179, 182, 215, 224, 238, 333, 335, 375, 376, 377, 391; 548/300, 356

[56] References Cited

U.S. PATENT DOCUMENTS

| 3,622,614 | 11/1971 | Nicolaides et al. | 260/470 |
| 3,978,045 | 8/1976 | Okamoto et al. | 260/239 B |

Primary Examiner—Richard Raymond
Attorney, Agent, or Firm—Oblon, Fisher, Spivak, McClelland & Maier

[57] ABSTRACT

N²-substituted-L-arginine esters and amides, and the pharmaceutically acceptable acid addition salts thereof have been found to be effective as pharmaceutical agents for the inhibition and suppression of thrombosis.

5 Claims, No Drawings

N²-SUBSTITUTED-L-ARGININE DERIVATIVES AND THE PHARMACEUTICALLY ACCEPTABLE ACID ADDITION SALTS THEREOF

This application is a divisional of application Ser. No. 703,704, filed July 8, 1976 which now issued to U.S. Pat. No. 4,069,325 of Jan. 17, 1978 which is a CIP of Ser. No. 671,436, filed Mar. 29, 1976, now U.S. Pat. No. 4,066,758, which is a divisional application of Ser. No. 622,390, filed Oct. 14, 1975, now abandoned.

BACKGROUND OF THE INVENTION

1. Field of the Invention

This invention relates to the discovery of certain new and useful N²-substituted-L-arginine derivatives and the pharmaceutically acceptable acid addition salts thereof, which are of especial value in view of their outstanding antithrombotic properties.

2. Description of the Prior Art

In the past, there have been many attempts to obtain new and improved agents for the treatment of thrombosis. Of these, N²-(p-tolylsulfonyl)-L-arginine esters are known to be effective in dissolving blood clots. (U.S. Pat. No. 3,622,615, issued Nov. 23, 1971)

However, there is a continuing need for a highly specific inhibitor on thrombin for the control of thrombosis. Accordingly, we have discovered novel N²-substituted-L-arginine derivatives which exhibit antithrombotic activity.

SUMMARY OF THE INVENTION

In summary, the compounds of this invention can be represented by the formula (I):

$$\begin{array}{c}HN\\ \phantom{H}\diagdown\\ \phantom{HN}C-N-(CH_2)_3-CHCOR\\ H_2N\phantom{\diagup}\phantom{XX}H\phantom{XXXX}|\\ \phantom{XXXXXXXXXXXXXX}HN-SO_2\\ \phantom{XXXXXXXXXXXXXXXXXXX}|\\ \phantom{XXXXXXXXXXXXXXXXXXX}R'\end{array} \quad (I)$$

wherein R is selected from the group consisting of (1)—$OR_1$, wherein $R_1$ is selected from the group consisting of $C_1$–$C_{10}$ alkyl, $C_3$–$C_{10}$ cycloalkyl, $C_1$–$C_{10}$ haloalkyl, $C_2$–$C_{10}$ alkoxyalkyl, $C_2$–$C_{10}$ alkenyl, $C_2$–$C_{10}$ alkynyl and $C_7$–$C_{15}$ aralkyl;

$$(2)-N\begin{array}{c}R_2\\ \diagdown\\ \diagup\\ R_3\end{array},$$

wherein $R_2$ and $R_3$ are selected from the group consisting of hydrogen, $C_1$–$C_{10}$ alkyl, $C_7$–$C_{15}$ aralkyl, and $C_1$–$C_{10}$ alkyl substituted with a group selected from $C_1$–$C_{10}$ alkoxy, $C_2$–$C_{10}$ alkoxycarbonyl and carboxy; and (3)—N⟨  ⟩Z, wherein Z is a divalent group which consists of two or more groups selected from methylene -CH₂- and monosubstituted methylene $$\begin{array}{c}R_4\\ |\\ -C-\\ |\\ H\end{array}$$

(wherein $R_4$ is selected from the group consisting of $C_1$–$C_{10}$ alkyl and $C_1$–$C_{10}$ alkoxy); and zero or one or more than one group selected from oxy -O-, thio -S-, alkyl substituted imino $$\begin{array}{c}R_5\\ |\\ -N-\end{array}$$

(wherein $R_5$ is $C_1$–$C_{10}$ alkyl) and acyl substituted imino $$\begin{array}{c}O=C-R_6\\ |\\ -N-\end{array}$$

(wherein $R_6$ is $C_1$–$C_{10}$ alkyl), which are combined in an arbitrary order, the number of the combined groups being up to 20; and R' is selected from the group consisting of

[naphthalene structure with OR″ and OR‴ substituents]

wherein R″ and R‴ when considered separately are $C_1$–$C_{10}$ alkyl, or R″ and R‴ when taken together are $C_1$–$C_{10}$ alkylene;

[series of fused bicyclic and tricyclic ring structures including indane, benzodioxole, benzodioxepine, benzodioxepine with R″″ substituent wherein R″″ is $C_1$–$C_{10}$ alkoxy; dibenzofuran (two isomers); xanthene; and dibenzodioxin]

and

Also encompassed within this invention are pharmaceutically acceptable acid addition salts thereof.

This invention also relates to a method for inhibiting activity and suppressing activation of thrombin in vivo, which comprises introducing into a living body a pharmaceutically effective amount of an N²-substituted-L-arginine ester or amide or the pharmaceutically acceptable acid addition salt thereof.

DETAILED DESCRIPTION OF THE PREFERRED EMBODIMENTS

As summarized above, this invention relates to a group of N²-substituted-L-arginine esters and amides of the formula (I):

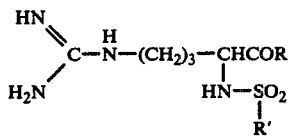     (I)

wherein R is represented by the formula (1)-OR₁,

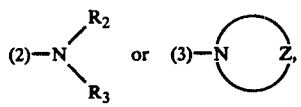

each of which will be described below in detail.

(1) In case where R is —OR₁

R₁ is selected from the group consisting of $C_1$–$C_{10}$ alkyl such as methyl, ethyl, propyl, isopropyl, butyl, tert-butyl, pentyl, hexyl or the like; $C_3$–$C_{10}$ cycloalkyl such as cyclopropyl, cyclohexyl or the like; $C_1$–$C_{10}$ haloalkyl such as 2-chloroethyl, 3-chloropropyl, 4-chlorobutyl or the like; $C_2$–$C_{10}$ alkoxyalkyl such as 2-methoxyethyl, 2-ethoxyethyl or the like; $C_2$–$C_{10}$ alkenyl such as allyl, 2-butenyl or the like; $C_2$–$C_{10}$ alkynyl such as 3-butynyl or the like; and $C_7$–$C_{15}$ aralkyl such as benzyl, phenethyl or the like.

(2) In case where R is

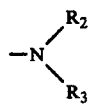

R₂ and R₃ are selected from the group consisting of hydrogen; $C_1$–$C_{10}$ alkyl such as methyl, ethyl, propyl, isopropyl, butyl, isobutyl, pentyl, hexyl, heptyl or the like; $C_7$–$C_{15}$ aralkyl such as benzyl, phenethyl, 3-phenylpropyl or the like; and $C_1$–$C_{10}$ alkyl substituted with a group selected from $C_1$–$C_{10}$ alkoxy, $C_2$–$C_{10}$ alkoxycarbonyl and carboxy such as 2-methoxyethyl, 3-methoxypropyl, 2-ethoxyethyl, ethoxycarbonylmethyl, 2-methoxycarbonylethyl, 2-ethoxycarbonylethyl, 3-ethoxycarbonylpropyl, carboxymethyl, 2-carboxyethyl or the like.

(3) In case where

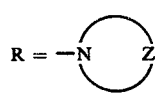

Z is a divalent group which consists of two or more groups selected from methylene -CH₂- and monosubstituted methylene

(wherein R₄ is selected from the group consisting of $C_1$–$C_{10}$ alkyl and $C_1$–$C_{10}$ alkoxy), and zero or one or more than one group selected from oxy -O-, thio -S-, alkyl substituted imino

(wherein R₅ is $C_1$–$C_{10}$ alkyl) and acyl substituted imino

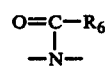

(wherein R₆ is $C_1$–$C_{10}$ alkyl), which are combined in an arbitrary order, the number of the combined groups being normally up to 20.

More particularly, R includes 1-polymethyleneiminyl groups or the derivatives thereof, such as 1-aziridinyl, 1-azetidinyl, 3-methoxy-1-azetidinyl, 3-ethoxy-1-azetidinyl, 1-pyrrolidinyl, piperidino, 4-methylpiperidino, 4-ethylpiperidino, 4-propylpiperidino, 4-isopropylpiperidino, 2-methylpiperidino, 3-methylpiperidino, 4-methoxypiperidino, 1-hexamethyleneiminyl, 1-octamethyleneiminyl, and the like; an oxazole or thiazole series such as 3-oxazolidinyl, 3-thiazolidinyl, and the like; an isoxazole or isothiazole series such as 2-isoxazolidinyl, 2-isothiazolidinyl, and the like; an oxazine series such as morpholino, 2,6-dimethylmorpholino, tetrahydro-1,3-oxazin-3-yl, and the like; a thiazine series such as tetrahydro-1,4-thiazin-4yl, and the like; 4-methyl-1-piperazinyl, 4-acetyl-1-piperazinyl, and the like. The preferred R groups are the following:

(1) In case where R is —OR₁ $C_1$–$C_8$ alkoxy, cyclohexyloxy, $C_2$–$C_6$ omega-chloroalkoxy, $C_2$–$C_6$ omega-alkoxyalkoxy, $C_3$–$C_6$ alkenyloxy, $C_2$–$C_6$ alkynyloxy, $C_7$–$C_9$ aralkyloxy (2) In case where R is

$C_1$–$C_9$ alkylamino, $C_2$–$C_6$ omega-alkoxyalkylamino, $C_3$–$C_8$ omega-alkoxycarbonylalkylamino, $C_7$–$C_{10}$ aralkylamino, $C_2$–$C_{10}$ dialkylamino (3) In case where R is

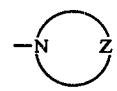

$C_3$–$C_{10}$ N,N-polymethyleneiminyl; $C_3$–$C_{10}$ N,N-polymethyleneiminyl substituted with a group selected from $C_1$–$C_5$ alkyl and $C_1$–$C_5$ alkoxy; tetrahydro-1, n-oxazin-n-yl (n=2, 3 or 4); tetrahydro-1, n-thiazin-n-yl (n=2,3 or 4); 1-piperazinyl substituted with a group selected from $C_1$–$C_5$ alkyl and $C_1$–$C_5$ acyl The most preferred R groups are the following:

(1) In case where R is —OR₁ propoxy, butoxy, hexyloxy, cyclohexyloxy, 3-chloropropoxy, 2-methoxyethoxy, 2-butenyloxy, 3-butynyloxy, benzyloxy (2) In case where R is

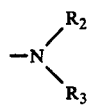

butylamino, 2-methoxyethylamino, 2-methoxycarbonylethylamino, 2-ethoxycarbonylethylamino, benzylamino, N-methyl-N-butylamino (3) In case where R is

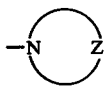

piperidino, hexamethyleneiminyl, 4-methylpiperidino, 4-ethylpiperidino, 4-methoxypiperidino, morpholino, tetrahydro-1,4-thiazin-4-yl, 4-methyl-1-piperazinyl, 4-acetyl-1-piperazinyl In the above formula (I), R' is a member selected from the group consisting of (a) substituted naphthyl

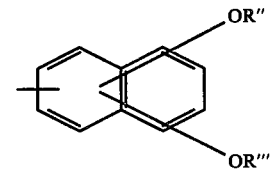

wherein R″ and R‴ when considered separately are respectively $C_1$–$C_{10}$ (preferably $C_1$–$C_5$) alkyl such as methyl, ethyl, propyl, isopropyl, butyl, isobutyl, tert-butyl or the like; or R″ and R‴ when taken together are $C_1$–$C_{10}$ (preferably $C_1$–$C_5$) alkylene such as methylene, ethylene, trimethylene or the like; the alkoxy (—OR″, —OR‴) or the alkylenedioxy (—OR″—R‴O—) group and the sulfonyl group may be located at any of the 1- to 8-position of the naphthalene nucleus; normally, the sulfonyl group is located at 1- or 2-position, and the alkylenedioxy group is a 6,7-alkylenedioxy group;

(b) 6-chromanyl 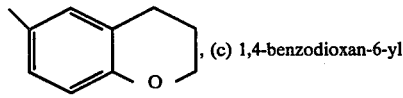, (c) 1,4-benzodioxan-6-yl

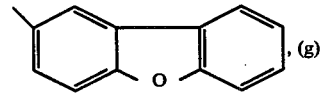, (d) 2H-3,4-dihydro-1,5-benzodioxepin-7-yl

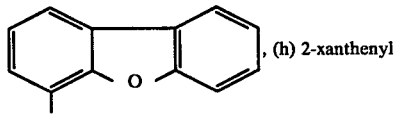, (e) derivatives of (d) having a substituent at the 3-position 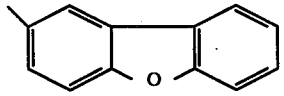 wherein R″″ is $C_1$–$C_{10}$ (preferably $C_1$–$C_5$) alkoxy, (f) 2-dibenzofuranyl 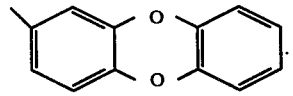, (g)

4-dibenzofuranyl, (h) 2-xanthenyl and (i) dibenzo-p-dioxin-2-yl.

Typical of the R' group are the following:

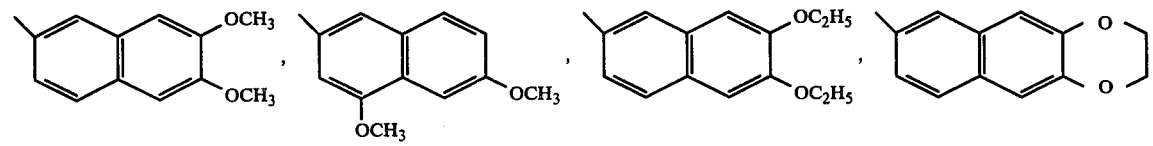

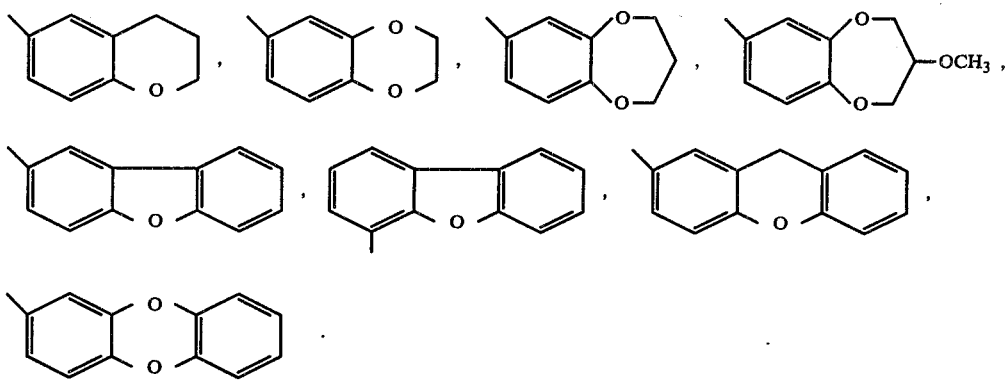

Illustrative of the typical N²-substituted-L-arginine esters and amides of this invention are the following:

(1) In the case of the ester derivatives
N²-(6,7-dimethoxy-2-naphthalenesulfonyl)-L-arginine propyl ester
N²-(6,7-dimethoxy-2-naphthalenesulfonyl)-L-arginine butyl ester
N²-(6,7-dimethoxy-2-naphthalenesulfonyl)-L-arginine benzyl ester
N²-(6,7-dimethoxy-2-naphthalenesulfonyl)-L-arginine 3-chloropropyl ester
N²-(6,7-dimethoxy-2-naphthalenesulfonyl)-L-arginine 2-methoxyethyl ester
N²-(6,7-dimethoxy-2-naphthalenesulfonyl)-L-arginine 3-butynyl ester
N²-(6,7-dimethoxy-2-naphthalenesulfonyl)-L-arginine 2-butenyl ester (2) In the case of the amide derivatives wherein R is

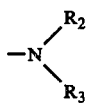

N²-(6,7-dimethoxy-2-naphthalenesulfonyl)-N-(2-methoxyethyl)-L-argininamide
N²-(6,7-dimethoxy-2-naphthalenesulfonyl)-N-benzyl-L-argininamide
N²-(2-xanthenesulfonyl)-N-methyl-N-butyl-L-argininamide (3) In the case of the amide derivatives wherein R is

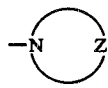

4-methyl-1-[N²-(6,7-dimethoxy-2-naphthalenesulfonyl)-L-arginyl]piperidine
4-ethyl-1-[N²-(6,7-dimethoxy-2-naphthalenesulfonyl)-L-arginyl]piperidine
1-[N²-(6,7-dimethoxy-2-naphthalenesulfonyl)-L-arginyl]hexamethyleneimine
4-[N²-(6,7-dimethoxy-2-naphthalenesulfonyl)-L-arginyl]morpholine
4-methoxy-1-[N²-(6,7-dimethoxy-2-naphthalenesulfonyl)-L-arginyl]piperidine
4-methyl-1-[N²-(4,6-dimethoxy-2-naphthalenesulfonyl)-L-arginyl]piperidine
4-ethyl-1-[N²-(4,6-dimethoxy-2-naphthalenesulfonyl)-L-arginyl]piperidine
4-ethyl-1-[N²-(2H-3,4-dihydro-1,5-benzodioxepin-7-sulfonyl)-L-arginyl]piperidine
4-methyl-1-[N²-(2H-3,4-dihydro-1,5-benzodioxepin-7-sulfonyl)-L-arginyl]piperidine
4-ethyl-1-[N²-(3-methoxy-(2H-3,4-dihydro-1,5-benzodioxepin)-7-sulfonyl)-L-arginyl]piperidine
4ethyl-1-[N²-(2-xanthenesulfonyl)-L-arginyl]piperidine
4-ethyl-1-[N²-(2-dibenzofuransulfonyl)-L-arginyl]piperidine
4-ethyl-1-[N²-(4-dibenzofuransulfonyl)-L-arginyl]piperidine
4-ethyl-1-[N²-(dibenzo-p-dioxin-2-sulfonyl)-L-arginyl]piperidine
1-[N²-(4-dibenzofuransulfonyl)-L-arginyl]hexamethyleneimine The following compounds are most preferred due to their high level of antithrombotic activity.
N²-(6,7-dimethoxy-2-naphthalenesulfonyl)-L-arginine butyl ester
N²-(6,7-dimethoxy-2-naphthalenesulfonyl)-N-(2-methoxyethyl)-L-argininamide
4-methyl-1-[N²-(6,7-dimethoxy-2-naphthalenesulfonyl)-L-arginyl]piperidine
4-ethyl-1-[N²-(6,7-dimethoxy-2-naphthalenesulfonyl)-L-arginyl]piperidine
4-methoxy-1-[N²-(6,7-dimethoxy-2-naphthalenesulfonyl)-L-arginyl]piperidine
4-methyl-1-[N²-(4,6-dimethoxy-2-naphthalenesulfonyl)-L-arginyl]piperidine
4-ethyl-1-[N²-(4,6-dimethoxy-2-naphthalenesulfonyl)-L-arginyl]piperidine
4-ethyl-1-[N²-(2-xanthenesulfonyl)-L-arginyl]piperidine
4-ethyl-1-[N²-(4-dibenzofuransulfonyl)-L-arginyl]piperidine
4-ethyl-1-[N²-(dibenzo-p-dioxin-2-sulfonyl)-L-arginyl]piperidine The pharmaceutically acceptable acid addition salts of the above compounds are of course also included within the scope of this invention.

The above compounds are intended only to illustrate the variety of structures which can be used in the process of this invention, and the above listing is not to be construed as limiting the scope of the invention.

These typical compounds are highly potent in their antithrombotic activity.

For the preparation of the compounds of this invention, various methods can be employed depending upon the particular starting materials and/or intermediates involved. Successful preparation of these compounds is possible by way of several synthetic routes which are outlined below.

(1) Preparation of $N^2$-substituted-L-arginine esters (a) Esterification of an $N^2$-substituted-L-arginine (i) Reaction of an $N^2$-substituted-L-arginine and an alcohol This process may be illustrated as follows:

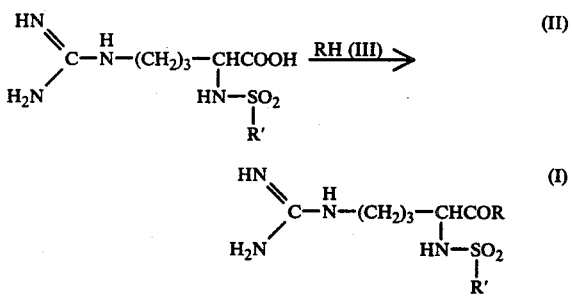

In the above formulas, R is $-OR_1$, in which $R_1$ is as defined herein above, and R' is as defined herein above.

The $N^2$-substituted-L-arginine ester (I) is prepared by esterifying an $N^2$-substituted-L-arginine (II) with an alcohol (III).

The esterification can be effected by reacting the $N^2$-substituted-L-arginine with at least 5 equivalents of the alcohol in the presence of at least an equimolar amount of an acid catalyst such as hydrogen chloride, sulfuric acid, toluenesulfonic acid or the like.

The reaction is generally carried out without an added solvent or in a suitable reaction-inert solvent at a temperature of 0° C. to the boiling temperature of the alcohol or the solvent for a period of 10 minutes to 15 hours. The preferred solvents are those which form an azeotropic mixture with water and facilitates the removal of water formed during the reaction.

Examples of such solvents are benzene, toluene, xylene, cyclohexane, carbon tetrachloride and dichloromethane.

After the reaction is complete, the alcohol and/or the solvent is distilled off to give the $N^2$-substituted-L-arginine ester (I) or an acid addition salt thereof, which can be purified by recrystallization from a combination of solvents such as ethyl ether, alcohols and acetone, or by reprecipitation by adding ether to the alcohol solution thereof.

The acid addition salt of the $N^2$-substituted-L-arginine ester can be easily converted to the corresponding ester by adjusting the pH of the solution.

(ii) Reaction of an $N^2$-substituted-L-arginine, an alcohol and a thionyl halide.

The $N^2$-substituted-L-arginine ester (I) can be prepared by reacting an $N^2$-substituted-L-arginine (II), an alcohol (III) and a thionyl halide such as thionyl chloride or thionyl bromide.

The thionyl halide is preferably used in an amount not less than 2 moles per mole of the $N^2$-substituted-L-arginine.

The other reaction conditions such as reaction temperature, reaction time, amount of the alcohol to be used; and the procedures of separation and purification of the product are as described above in the esterification with an acid catalyst.

According to this method, the product is usually a halogeno acid salt of the $N^2$-substituted-L-arginine ester.

The $N^2$-substituted-L-arginine (II) can be esterified by many other procedures.

The $N^2$-substituted-L-arginines (II) starting materials are readily obtained by reacting arginine and a sulfonyl halide (preferably a chloride) of the formula (IV):

wherein R' is as defined herein above and X is halogen, in the presence of a base such as $K_2CO_3$, KOH, NaOH, triethylamine or pyridine.

(b) Condensation of an L-arginine ester with a sulfonyl halide

This process may be illustrated as follows:

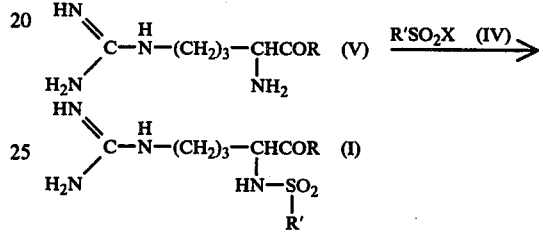

In the above formulas, R is $-OR_1$ wherein $R_1$ is as defined herein above; R' is as defined herein above; and X is halogen.

The $N^2$-substituted-L-arginine ester (I) is prepared by the condensation of an L-arginine ester (V) with a substantially equimolar amount of a sulfonyl halide (IV), preferably a chloride.

The condensation reaction is generally effected in a suitable reaction-inert solvent in the presence of an excess of a base, such as an organic base (triethylamine, pyridine) or a solution of an inorganic base (sodium hydroxide, potassium carbonate), at a temperature of 0° C. to the boiling temperature of the solvent for a period of 10 minutes to 15 hours.

The preferred solvents for the condensation include dichloromethane, diethyl ether-water and dioxane-water.

After the reaction is complete, the formed salt is extracted with water, and the solvent is removed by such standard means as evaporation under reduced pressure to give the $N^2$-substituted-L-arginine ester (I), which can be purified by trituration or recrystallization from a suitable solvent, such as diethyl ether-tetrahydrofuran, diethyl ether-methanol and water-methanol, or may be chromatographed on silica gel.

The L-arginine ester (V) starting materials are most generally prepared by reacting L-arginine with an alcohol in the presence of an acid catalyst.

(2) Preparation of $N^2$-substituted-L-argininamides (a) Condensation of an L-argininamide with a sulfonyl halide This process may be illustrated as follows:

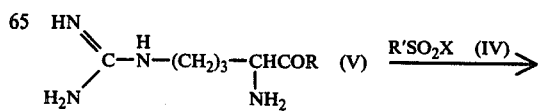

-continued

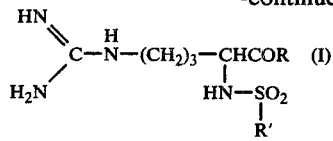

In the above formulas, R is

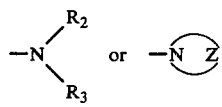

wherein $R_2$, $R_3$ and Z are as defined herein above; R' is as defined herein above; and X is halogen. The $N^2$-substituted-L-argininamide (I) is prepared by condensing an L-argininamide (V) with a substantially equimolar amount of a sulfonyl halide (IV), preferably a chloride, in the presence of a base.

The reaction conditions are the same as those described in the Process (1)(b) (condensation of an L-arginine ester with a sulfonyl halide).

The L-argininamides (V) starting materials required for the condensation reaction can be prepared by protecting the guanidino and α-amino group of the arginine via nitration, acetylation, formylation, phthaloylation, trifluoroacetylation, p-methoxybenzyloxycarbonylation, benzoylation, benzyloxycarbonylation, tert-butoxycarbonylation or tritylation and then condensing the formed $N^G$-substituted-$N^2$-substituted-L-arginine with a corresponding amine by such a conventional process as the acid chloride method, azide method, mixed anhydride method, activated ester method or carbodiimide method, and thereafter selectively removing the protective group.

(b) Removal of the $N^G$-substituent from an $N^G$-substituted-$N^2$-substituted-L-argininamide This process may be illustrated as follows:

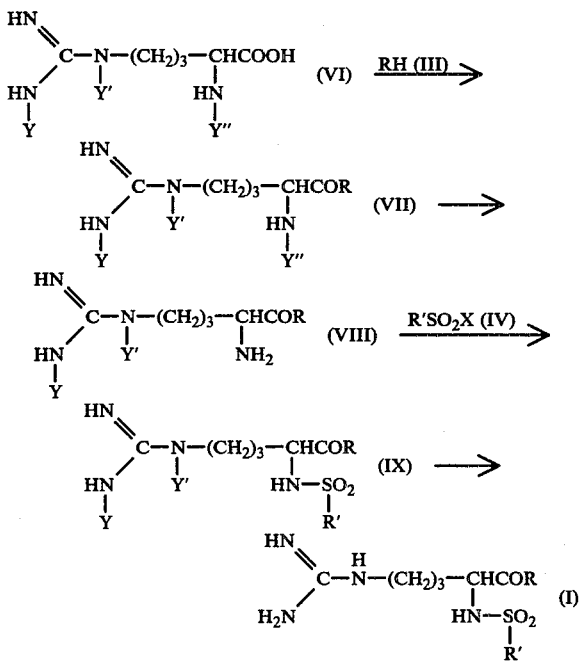

In the above formulas, R is

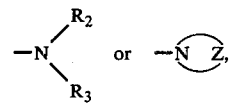

wherein $R_2$, $R_3$ and Z are as defined herein above; R' is as defined herein above; X is halogen; Y" is a protective group for the amino group, such as benzyloxycarbonyl or tert-butoxycarbonyl; and Y and Y' are hydrogen and protective groups for the guanidino group, such as nitro, tosyl, trityl, oxycarbonyl or the like.

At least one of Y and Y' is a protective group for the guanidino group.

The $N^2$-substituted-L-argininamide (I) is prepared by removing the $N^G$-substituent from an $N^G$-substituted-$N^2$-substituted-L-argininamide (IX) by means of acidolysis or hydrogenolysis.

The acidolysis is generally effected by contacting the $N^G$-substituted-$N^2$-substituted-L-argininamide (IX) and an excess of an acid such as hydrogen fluoride, hydrogen chloride, hydrogen bromide or trifluoroacetic acid, without a solvent or in a solvent, such as an ether (tetrahydrofuran, dioxane), an alcohol (methanol, ethanol) or acetic acid at a temperature of $-10°$ C. to $100°$ C., and preferably at room temperature for a period of 10 minutes to 24 hours.

The products are isolated by evaporation of the solvent and the excess acid, or by trituration with a suitable solvent followed by filtration and drying.

Because of the use of the excess acid, the products are generally the acid addition salts of the $N^2$-substituted-L-argininamides (I), which can be easily converted to a free amide by neutralization.

The removal of the nitro group and the oxycarbonyl group, e.g., benzyloxycarbonyl, p-nitrobenzyloxycarbonyl, is readily accomplished by the hydrogenolysis.

The hydrogenolysis is effected in a reaction-inert solvent, e.g., methanol, ethanol, tetrahydrofuran or dioxane, in the presence of a hydrogen-activating catalyst, e.g., Raney nickel, palladium, or platinum, in a hydrogen atmosphere at a temperature of $0°$ C. to the boiling temperature of the solvent for a period of 2 hours to 120 hours.

The hydrogen pressure is not critical, and atmospheric pressure is sufficient.

The $N^2$-substituted-L-argininamides (I) are isolated by filtration of the catalyst followed by evaporation of the solvent.

The $N^2$-substituted-L-argininamides can be purified in the same manner as described above.

The $N^G$-substituted-$N^2$-substituted-L-argininamides (IX) starting materials can be prepared by condensing an $N^G$-substituted-$N^2$-substituted-L-arginine (VI) (generally the $N^2$-substituent is a protective group for the amino group, such as benzyloxycarbonyl, tert-butoxycarbonyl, or the like) and a corresponding amine (III) via the azide method, mixed anhydride method, activated ester method, carbodiimide method or the like, selectively removing only the $N^2$-substituent of an $N^G$-substituted-$N^2$-substituted-L-argininamide (VII) by means of catalytic hydrogenolysis or acidolysis, and then condensing the thus obtained $N^G$-substituted-L-argininamide (VIII) with a sulfonyl halide (IV), preferably a chloride in the presence of a base in a solvent. These reaction conditions are as described above in the condensation of an L-argininamide with a sulfonyl halide, and the removal of the $N^G$-substituent from an $N^G$-substituted-$N^2$-substituted-L-argininamide.

(c) Condensation of an $N^2$-substituted-L-arginyl halide with an amine

This process may be illustrated as follows:

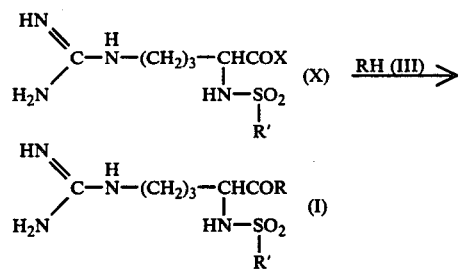

In the above formulas, R is

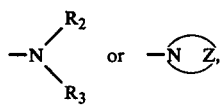

wherein $R_2$, $R_3$ and Z are as defined herein above; R' is as defined herein above; and X is halogen. The $N^2$-substituted-L-argininamide (I) is prepared by the condensation of an $N^2$-substituted-L-arginyl halide (X), preferably a chloride with at least an equimolar amount of an amine (III).

The condensation reaction can be carried out without an added solvent. However, satisfactory results will be obtained with the use of a solvent such as basic solvents (dimethylformamide, dimethylacetamide, etc.) or halogenated solvents (chloroform, dichloromethane, etc.)

The amount of the solvent to be used is not critical and may vary from about 5 to 100 times the weight of the $N^2$-substituted-L-arginyl halide (X).

Preferred condensation reaction temperatures are in the range of from $-10°$ C. to room temperature. The reaction time is not critical, but varies with the amine (III) employed. In general, a period of from 5 minutes to 10 hours is operable.

The obtained $N^2$-substituted-L-argininamide can be isolated and purified in the same manner as described above.

The $N^2$-substituted-L-arginyl halide (X) starting materials required for the condensation reaction can be prepared by reacting an $N^2$-substituted-L-arginine (II) with at least an equimolar amount of a halogenating agent such as thionyl chloride, phosphorous oxychloride, phosphorus trichloride, phosphorous pentachloride or phosphorus tribromide. The halogenation can be carried out with or without an added solvent.

The preferred solvents are chlorinated hydrocarbons such as chloroform and dichloromethane, and ethers such as tetrahydrofuran and dioxane.

The amount of the solvent to be used is not critical and may vary from about 5 to 100 times the weight of the $N^2$-substituted-L-arginine. Preferred reaction temperatures are in the range of $-10°$ C. to room temperature. The reaction time is not critical, but varies with the halogenating agent and reaction temperature. In general, a period of 15 minutes to 5 hours is operable.

(d) Guanidylation of an $N^2$-substituted-L-ornithinamide or an acid addition salt thereof This process may be illustrated as follows:

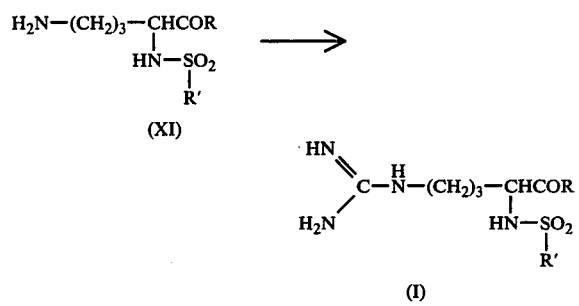

In the above formulas, R is

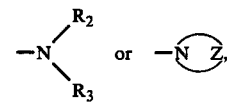

wherein $R_2$, $R_3$ and Z are as defined herein above; and R' is as defined herein above.

The $N^2$-substituted-L-argininamide (I) is prepared by guanidylating an $N^2$-substituted-L-ornithinamide (XI) with an ordinary guanidylating agents such as an O-alkylisourea, S-alkylisothiourea, 1-guanyl-3,5-dimethylpyrazole or carbodiimide. The preferred guanidylating agents are the O-alkylisourea and the S-alkylisothiourea.

The guanidylation of the $N^2$-substituted-L-ornithinamide (XI) with the O-alkylisourea or S-alkylisothiourea is generally effected in a solvent in the presence of a base at a temperature of from $0°$ C. to the boiling temperature of the solvents for a period of from 30 minutes to 50 hours.

Examples of the preferred base are triethylamine, pyridine, sodium hydroxide and sodium methoxide. The base is used in an amount of 0.01 to 0.1 equivalent to the $N^2$-substituted-L-ornithinamide. Examples of the preferred solvent are water, water-ethanol and water-dioxane.

After the reaction is complete, the $N^2$-substituted-L-argininamide (I) is isolated by evaporation of the solvent followed by removal of the excess base and the formed salt by a water wash.

(e) Reaction of an $N^2$-substituted-L-arginine ester and a primary amine p This process may be illustrated as follows:

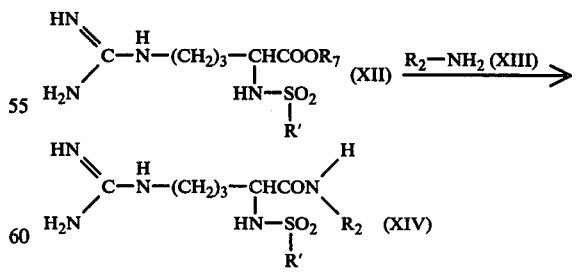

In the above formulas, $R_2$ and R' are as defined herein above; and $R_7$ is $C_1$-$C_{10}$ alkyl.

The $N^2$-substituted-L-argininamide represented by the formula (XIV) can be prepared by the reaction of an $N^2$-substituted-L-arginine ester (XII) and about 2 to 10 equivalents of a primary amine (XIII).

The reaction is generally carried out without an added solvent or in a solvent such as an alcohol (methanol, ethanol), an ether (ethyl ether, tetrahydrofuran), a hydrocarbon (benzene, toluene), a halogenated hydrocarbon (chloroform, dichloromethane) or water at room temperature for a period of several hours to several days. In order to accelerate the reaction, the reaction mixture may be heated to a temperature of up to the boiling point of the amine or the solvent. Alternatively, a basic catalyst such as sodium methoxide or pyridine may be added to the reaction mixture.

After the reaction is complete, the formed $N^2$-substituted-L-argininamide (XIV) is isolated by filtration or by evaporation of the excess amine and/or the solvent, washed with water, and then purified by recrystallization from a suitable solvent such as water-methanol.

The $N^2$-substituted-L-arginine esters or amides (I) of this invention form acid addition salts with any of a variety of inorganic and organic acids. The product of the reactions described above can be isolated in the free form or in the form of acid addition salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. Likewise, treatment of the acid addition salts with a base results in a regeneration of the free amide or ester.

As stated above, the $N^2$-substituted-L-arginine esters and amides, and the salts thereof of this invention are characterized by highly specific inhibitory activity against thrombin, and therefore, these compounds are useful in the determination of thrombin in blood as diagnostic reagents, and/or for the medical control or prevention of thrombosis. The antithrombotic activities of the $N^2$-substituted-L-arginine esters and amides of this invention were compared with that of a known antithrombotic agent, $N^2$-(p-tolylsulfonyl)-L-arginine methyl ester, by determining the fibrinogen congulation time. The measurement of the fibrinogen coagulation time was conducted as follows: An 0.8 ml aliquot of a fibrinogen solution, which has been prepared by dissolving 150 mg of bovine fibrinogen (Cohn fraction 1) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath. Immediately after mixing, the reaction mixture was transferred from the ice bath to a bath maintained at 25° C. Coagulation times were taken as the period between the time of transference to the 25° C. bath and the time of the first appearance of fibrin threads. In the cases where no drug samples were added, the coagulation time was 50-55 seconds.

The experimental results are summarized in TABLE 1. The term "concentration required to prolong the coagulation time by a factor of two" is the concentration of an active ingredient required to prolong the normal coagulation time of 50-55 seconds to 100-110 seconds.

The concentration required to prolong the coagulation time by a factor of two for the known antithrombotic agent, $N^2$-(p-tolysulfonyl)-L-arginine methyl ester, was 1,100 μM.

The inhibitors are shown in TABLE 1 by indicating R and R' in the formula (1) and the addition moiety.

When a solution containing an $N^2$-substituted-L-arginine ester or amide of this invention was administered intravenously into animal bodies, the high antithrombotic activity in the circulating blood was maintained for from one to three hours. The half-life for decay of the antithrombotic compounds of this invention in circulating blood was shown to be approximately 30 minutes; the physiological conditions of the host animals (rat, rabbit, dog and chimpanzee) were well maintained. The experimental decrease of fibrinogen in animals caused by infusion of thrombin was satisfactorily controlled by simultaneous infusion of the compounds of this invention:

The acute toxicity values ($LD_{50}$) determined by oral administration of substances of formula (I) in mice (male, 20 g) range from about 1,000 to 10,000 milligrams per kilogram of body weight. The therapeutic agents of this invention may be administered alone or in combination with pharmaceutically acceptable carriers, the proportion of which is determined by the solubility and chemical nature of the compound, chosen route of administration and standard pharmaceutical practice. For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents. Physicians will determine the dosage of the present therapeutic agents which will be most suitable, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally. The therapeutic dosage is generally 10–50 mg/kg of active ingredient parenterally, 10–500 mg/kg orally per day.

Having generally described the invention, a more complete understanding can be obtained by reference to certain specific examples, which are included for purposes of illustration only and are not intended to be limiting unless otherwise specified.

EXAMPLE 1

To 1.0 g (0.0018 mole) of 4-ethyl-1-[$N^G$-nitro-$N^2$-(6,7-dimethoxy-2-naphthalenesulfonyl)-L-arginyl]-piperidine were added 5.7 g (0.0053 mole) of anisole and 3 ml of hydrogen fluoride while cooling with Dry-ice-/acetone, and the mixture was stirred for 30 minutes in an ice bath. The anisole and the excess hydrogen fluoride were evaporated at reduced pressure with cooling to afford an oily product, which was slurried with 100 ml of dry ethyl ether. The ether layer was separated by decantation, and the obtained powder was dissolved in methanol, reprecipitated with ethyl ether, and then filtered to give 4-ethyl-1-[$N^2$-(6,7-dimethoxy-2-naphthalenesulfonyl)-L-arginyl]piperidine hydrofluoride in the powder form in a yield of 75%.

| Elemental analysis: as $C_{25}H_{37}O_5N_5S \cdot HF$ | | | |
|---|---|---|---|
|  | C | H | N |
| Calculated (%) | 55.64 | 7.10 | 12.98 |
| Found (%) | 55.50 | 7.12 | 12.87 |

EXAMPLE 2

Into a suspension of 1.0 g (0.00186 mole) of 4-[$N^G$-nitro-$N^2$-(6,7-dimethoxy-2-naphthalenesulfonyl)-L-arginyl] morpholine and 0.1 g of palladium black in 30 ml of ethanol and 10 ml of acetic acid was passed hydrogen gas for 60 hours at room temperature. Upon completion of the reaction, the catalyst was filtered off, and the solvent was evaporated under reduced pressure to give a viscous oily residue, which was taken up in methanol and reprecipitated with ether to afford 4-[$N^2$-(6,7-dimethoxy-2-naphthalenesulfonyl)-L-arginyl] morpholine acetate in the powder form in a yield of 82%.

| Elemental analysis: as $C_{22}H_{31}O_6N_5S \cdot CH_3COOH$ | | | |
|---|---|---|---|
|  | C | H | N |
| Calculated (%) | 52.07 | 6.37 | 12.65 |
| Found (%) | 51.99 | 6.28 | 12.41 |

EXAMPLE 3

Into a suspension of 2.0 g (0.0027 mole) of $N^G,N^G$-dibenzyloxycarbonyl-$N^2$-(6,7-dimethoxy-2-naphthalenesulfonyl)-N-butyl-L-argininamide and 20% palladium-carbon in 50 ml of ethanol and 10 ml of acetic acid was passed hydrogen gas for 10 hours at room temperature. Upon completion of the reaction, the catalyst was filtered off, and the solvent was evaporated under reduced pressure to give an oily residue, which was reprecipitated with methanol-ether to give $N^2$-(6,7-dimethoxy-2-naphthalenesulfonyl)-N-butyl-L-argininamide acetate in the powder form in a yield of 78%.

| Elemental analysis: as $C_{22}H_{33}O_5N_5S \cdot CH_3COOH$ | | | |
|---|---|---|---|
|  | C | H | N |
| Calculated (%) | 53.42 | 6.91 | 12.98 |
| Found (%) | 53.61 | 6.87 | 12.71 |

EXAMPLE 4

To 5.0 ml (0.069 mole) of cold thionyl chloride was added with vigorous stirring 1.0 g (0.00236 mole) of $N^2$-(6,7-dimethoxy-2-naphthalenesulfonyl)-L-arginine, and the reaction mixture was allowed to react at room temperature for 1 hour. After the reaction was complete, 100 ml of dry ether was added to the reaction mixture, and the formed precipitate was collected and washed well with 50 ml of dry ether.

The thus obtained powdery $N^2$-(6,7-dimethoxy-2-naphthalenesulfonyl)-L-arginyl chloride dihydrochloride was added with stirring to a solution of 1.2 g (0.012 mole) of 4-methyl-piperidine in 10 ml of chloroform, and the mixture was allowed to stand for 3 hours at room temperature. After the reaction was complete, the solvent and the excess 4-methylpiperidine were distilled under reduced pressure, and the residue was dissolved in 20 ml of chloroform. The chloroform layer was washed well with saturated NaCl aqueous solution and dried over sodium sulfate, and then, the chloroform was distilled under reduced pressure. Addition of 10 ml of acetic acid and 100 ml of dry ether to the residue resulted in deposition of an oily product. The ether was removed by decantation, and the oily product was washed well with dry ether to give powdery 4-methyl-1-[$N^2$-(6,7-dimethoxy-2-naphthalenesulfonyl)-L-arginyl]piperidine monoacetate. Yield 1.1 g (84%).

| Elemental analysis: as $C_{24}H_{35}N_5O_5S \cdot CH_3COOH$ | | | |
|---|---|---|---|
|  | C | H | N |
| Calculated (%) | 55.21 | 6.95 | 12.38 |
| Found (%) | 55.11 | 6.74 | 12.01 |

EXAMPLE 5

To a suspension of 1.00 g (0.00236 mole) of $N^2$-(6,7-dimethoxy-2-naphthalenesulfonyl)-L-arginine in 20 ml of tetrahydrofuran was added little by little 0.98 g (0.0047 mole) of phosphorus pentachloride while cooling with ice water. The mixture was stirred for 1 hour at 0°–5° C., and then, for 2 hours at room temperature. To this reaction mixture was added 100 ml of dry ether, and the supernatant was removed by decantation. The residual oily product was washed with 50 ml of dry ether to give powdery $N^2$-(6,7-dimethoxy-2-naphthalenesulfonyl)-L-arginyl chloride dihydrochloride, which was added with stirring to a solution of 1.31 g (0.015 mole) of N-methyl-N-butylamine in 10 ml of chloroform. Thereafter, following the same procedures as described in Example 1, $N^2$-(6,7-dimethoxy-2-naphthalenesulfonyl)-N-methyl-N-butyl-L-argininamide monoacetate was obtained. Yield 0.76 g (58%).

| Elemental analysis: as $C_{23}H_{35}N_5O_5S \cdot CH_3COOH$ | | | |
|---|---|---|---|
|  | C | H | N |
| Calculated (%) | 54.24 | 7.10 | 12.65 |
| Found (%) | 54.00 | 7.21 | 12.46 |

EXAMPLE 6

To a solution of 1.0 g (0.004 mole) of L-arginine ethyl ester dihydrochloride in 50 ml of dichloromethane and 1.15 g (0.012 mole) of triethylamine was added 1.14 g (0.004 mole) of 4,6-dimethoxy-2-naphthalenesulfonyl chloride with stirring at room temperature.

After stirring for 5 hours at room temperature, the reaction mixture was washed with water to remove the formed triethylamine hydrochloride. After the solution was dried over sodium sulfate, the dichloromethane was evaporated under reduced pressure, to give $N^2$-(4,6-dimethoxy-2-naphthalenesulfonyl)-L-arginine ethyl ester.

To this product was added ethyl ether, and then hydrogen chloride was passed. The formed precipitate was filtered to give $N^2$-(4,6-dimethoxy-2-naphthalenesulfonyl)-L-arginine ethyl ester hydrochloride in the form of a powder. Yield 84%.

| Elemental analysis: as $C_{20}H_{29}O_6N_4SCl$ | | | |
|---|---|---|---|
|  | C | H | N |
| Calculated (%) | 49.13 | 5.97 | 11.46 |
| Found (%) | 48.96 | 6.15 | 11.52 |

EXAMPLE 7

To a suspension of 1.50 g (0.005 mole) of L-arginine butyl ester dihydrochloride in a solution consisting of 1.4 g of potassium carbonate and 10 ml of water, which had been cooled to 0–5° C, was added dropwise of 1.43 g (0.005 mole) of 6,7-dimethoxy-2-naphthalenesulfonyl chloride in 10 ml of ethyl ether with vigorous stirring over a period of 30 minutes.

The mixture was stirred for further 10 minutes and a viscous deposit was obtained. The solvent was removed by decantation, and the residual deposit was washed with water and ether.

To a suspension of the resulting product in 20 ml of ethyl ether was added 2 g of p-toluenesulfonic acid morohydrate with stirring to yield a crystal, which was filtered and washed several times with ethyl ether to give $N^2$-(6,7-dimethoxy-2-naphthalenesulfonyl)-L-arginine butyl ester p-toluenesulfonate in 92% yield; m.p. 113°–115° C.

| Elemental analysis: as $C_{29}H_{40}O_9N_4S_2$ | | | |
|---|---|---|---|
| | C | H | N |
| Calculated (%) | 53.36 | 6.18 | 8.59 |
| Found (%) | 53.23 | 6.14 | 8.70 |

EXAMPLE 8

To a mixture of 1.00 g (0.0037 mole) of 4-ethyl-1-(L-arginyl) piperdine and 0.61 g (0.0044 mole) of potassium carbonate in 10 ml of water, which had been cooled to 0° C., was added dropwise a solution of 1.25 g (0.0044 mole) of 6.7-dimethoxy-2-naphthalenesulfonyl chloride in 30 ml of dioxane with vigorous stirring over a period of 30 minutes. The reaction mixture was stirred for additional 5 hours at room temperature and the formed precipitate was removed by filtration. The solvent was evaporated under reduced pressure, and to the residue was added 50 ml of chloroform. The undissolved material was filtered off and the solution was dried over sodium sulfate. Addition of 10 ml of acetic acid to this solution followed by evaporation of the solvent gave a viscous oily product, which was reprecipitated with methanol-ethyl ether to afford 4-ethyl-1-[$N^2$-(6,7-dimethoxy-2-naphthalenesulfonyl)-L-arginyl]piperidine acetate in a 62% yield.

| Elemental analysis: as $C_{24}H_{35}O_7N_5S$ | | | |
|---|---|---|---|
| | C | H | N |
| Calculated (%) | 55.01 | 7.28 | 12.34 |
| Found (%) | 54.93 | 7.14 | 12.28 |

EXAMPLE 9

To a solution of 1.00 g (0.0041 mole) of 4-(L-arginyl) morpholine in 50 ml of chloroform and 0.52 g (0.0052 mole) of triethylamine was added 1.48 g (0.0052 mole) of 6,7-dimethoxy-2-naphthalenesulfonyl chloride with stirring at room temperature.

After stirring for 5 hours at room temperature, the reaction mixture was slurried with 10 ml of water.

The aqueous layer was separated, and the residual chloroform layer was dried over sodium sulfate. Addition of 2 ml of acetic acid to the chloroform layer followed by evaporation of chloroform gave a viscous oily residue, which was reprecipitated with methanol-ethyl ether to afford 4-[$N^2$-(6,7-dimethoxy-2-naphthalenesulfonyl)-L-arginyl]morpholine acetate in a 66% yield.

| Elemental analysis: as $C_{21}H_{29}O_8N_5S$ | | | |
|---|---|---|---|
| | C | H | N |
| Calculated (%) | 52.07 | 6.37 | 12.65 |
| Found (%) | 51.88 | 6.26 | 12.26 |

EXAMPLE 10

To a suspension of 1.0 g of $N^2$-(4,6-dimethoxy-2-naphthalenesulfonyl)-L-arginine in 30 ml of ethanol was added little by little 1 ml of thionyl chloride with stirring. The suspension soon became a clear solution. After the solution was refluxed with stirring for 4 hours, the ethanol was distilled away under reduced pressure, to give a viscous oily residue, which was washed well three times with 20 ml of ethyl ether to afford colorless and powdery $N^2$-(4,6-dimethoxy-2-naphthalenesulfonyl)-L-arginine ethyl ester hydrochloride in a 96% yield.

| Elemental analysis: as $C_{20}H_{29}O_6N_4SCl$ | | | |
|---|---|---|---|
| | C | H | N |
| Calculated (%) | 49.13 | 5.97 | 11.46 |
| Found (%) | 48.96 | 6.15 | 11.52 |

EXAMPLE 11

A mixture of 1.0 g of $N^2$-(6,7-dimethoxy-2-naphthalenesulfonyl)-L-arginine and 1.0 g of p-toluenesulfonic acid monohydrate in 5 ml of butyl alcohol and 30 ml of benzene was refluxed for 5 hours, while removing the water formed during the reaction. The reaction mixture was concentrated under reduced pressure, and to the residue was added ethyl ether to yield a crystalline substance which was collected by filtration, washed several times with ethyl ether to afford $N^2$-(6,7-dimethoxy-2-naphthalenesulfonyl)-L-arginine butyl ester p-toluenesulfonate: yield 92%, m.p. 113-115° C.

| Elemental analysis: as $C_{29}H_{40}O_9N_4S_2$ | | | |
|---|---|---|---|
| | C | H | N |
| Calculated (%) | 53.36 | 6.18 | 8.59 |
| Found (%) | 53.23 | 6.14 | 8.70 |

EXAMPLE 12

To 1.2 g (0.0020 mole) of 4-ethyl-1-[$N^G$-nitro-$N^2$-(6-chromansulfonyl)-L-arginyl]piperidine was added 0.64 g (0.0060 mole) of anisole and 3 ml of hydrogen fluride while cooling with Dry-ice/acetone, and the mixture was stirred for 30 minutes in an ice bath. The excess hydrogen fluoride was evaporated at reduced pressure with cooling to afford an oily product, which was slurried with 100 ml of dry ethyl ether. The ether layer was separated by decantation, and the obtained powder was dissolved in methanol, reprecipitated with ethyl ether, and then filtered to give 4-ethyl-1-[$N^2$-(6-chromansulfonyl)-L-arginyl]piperidine hydrofluoride in the powder form in a yield of 63%.

| Elemental analysis: as $C_{22}H_{36}O_4N_5S \cdot HF$ | | | |
|---|---|---|---|
| | C | H | N |
| Calculated (%) | 54.41 | 7.47 | 14.42 |

| Elemental analysis: as $C_{22}H_{36}O_4N_5S \cdot HF$ | | | |
|---|---|---|---|
| | C | H | N |
| Found (%) | 54.70 | 7.45 | 14.31 |

EXAMPLE 13

Into a suspension of 1.2 g (0.0020 mole) of 4-ethyl-1-[$N^G$-nitro-$N^2$-(1,4-benzodioxane-6-sulfonyl)-L-arginyl]piperidine and 0.1 g of palladium black in 30 ml of ethanol and 10 ml of acetic acid was passed hydrogen gas for 30 hours at room temperature. Upon completion of the reaction, the catalyst was filtered off, and the solvent was evaporated under reduced pressure to give a viscous oily residue, which was taken up in methanol and reprecipitated with ethyl ether to afford 4-ethyl-1-[$N^2$-(1,4-benzodioxane-6-sulfonyl)-L-arginyl]piperidine acetate in the powder form in a yield of 85%.

| Elemental analysis: as $C_{21}H_{33}O_5N_5S \cdot CH_3COOH$ | | | |
|---|---|---|---|
| | C | H | N |
| Calculated (%) | 52.35 | 17.07 | 13.27 |
| Found (%) | 52.65 | 7.01 | 13.12 |

EXAMPLE 14

Into a suspension of 2.0 g (0.0026 mole) of 4-ethyl-1-[$N^G$, $N^G$-dibenzyloxycarbonyl-$N^2$-(2H-3,4-dihydro-1,5-benzodioxepin-7-sulfonyl)-L-arginyl]piperidine and 10% palladium-carbon in 50 ml of ethanol and 10 ml of acetic acid was passed hydrogen gas for 10 hours at room temperature. Upon completion of the reaction, the catalyst was filtered off, and the solvent was evaporated under reduced pressure to give a viscous oily residue, which was reprecipitated with methanol-ether to give 4-ethyl-1-[$N^2$-(2H-3,4-dihydro-1,5-benzodioxepin-7-sulfonyl)-L-arginyl]piperidine acetate in the powder form in a yield of 81%.

| Elemental analysis: as $C_{24}H_{39}O_7N_5S \cdot CH_3COOH$ | | | |
|---|---|---|---|
| | C | H | N |
| Calculated (%) | 53.22 | 7.26 | 12.93 |
| Found (%) | 53.51 | 7.04 | 12.87 |

Various other $N^2$-substituted-L-arginine esters and amides were synthesized in accordance with the procedures of the above examples. The results, including those of the above examples, are summarized in TABLE 1. In TABLE 1, $N^2$-substituted-L-arginine esters and amides represented by the general formula (I) are shown by indicating R and R' in the formula and addition moieties.

TABLE 1
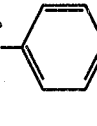
| No. | R | Addition Moiety | Concentration required to prolong the coagulation time by a factor of two (μM) | Preparation process (Ex. No.) | Property or m.p. (° C) | Elemental analysis Upper: Calculated Lower: Found | | | I.R. (KBr) (cm⁻¹) |
|---|---|---|---|---|---|---|---|---|---|
| | | | | | | C | H | N | |
| 1 | —O-n-C₃H₇ | 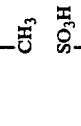 | 1.0 | 11 | 130–133 | 52.66<br>52.57 | 6.00<br>5.89 | 8.77<br>8.66 | |
| 2 | —O-n-C₄H₉ |  | 0.2 | 7 | 113–115 | 53.36<br>53.23 | 6.18<br>6.14 | 8.59<br>8.70 | |
| 3 | —O-n-C₆H₁₃ | 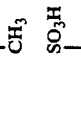 | 0.6 | 11 | 107–112 | 54.70<br>54.83 | 6.51<br>6.40 | 8.23<br>8.29 | |
| 4 | 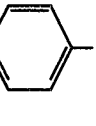 | 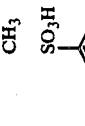 | 0.35 | 11 | powder | 55.48<br>55.36 | 5.53<br>5.29 | 8.09<br>8.19 | |
| 5 | —OCH₂CH₂CH₂Cl | 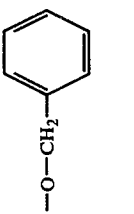 | 0.15 | 11 | 100–105 | 49.96<br>49.89 | 5.54<br>5.39 | 8.32<br>8.49 | |

TABLE 1-continued

Structure: HN=C(NH₂)−N(H)−(CH₂)₃−CH(NHSO₂R')−COR

| No. | R | R' | Addition Moiety | Concentration required to prolong the coagulation time by a factor of two (μM) | Preparation process (Ex. No.) | Property or m.p. (° C) | Elemental analysis Upper: Calculated Lower: Found | | | I.R. (KBr) (cm⁻¹) |
|---|---|---|---|---|---|---|---|---|---|---|
| | | | | | | | C | H | N | |
| 6 | cyclohexyl−O− | 3,2-dimethoxy-6-methylnaphthyl | p-SO₃H-C₆H₄-CH₃ | 15 | 11 | 125−130 | 54.86<br>54.69 | 6.24<br>6.22 | 8.25<br>8.31 | |
| 7 | −O−CH₂CH₂OCH₃ | 3,2-dimethoxy-6-methylnaphthyl | p-SO₃H-C₆H₄-CH₃ | 0.25 | 11 | 104−107 | 51.37<br>51.44 | 5.85<br>5.76 | 5.36<br>8.57 | |
| 8 | −O−CH₂CH₂C≡CH | 3,2-dimethoxy-6-methylnaphthyl | p-SO₃H-C₆H₄-CH₃ | 1.5 | 11 | 127−131 | 53.69<br>53.54 | 5.59<br>5.32 | 8.64<br>8.46 | |
| 9 | −O−CH₂CH=CHCH₃ | 3,2-dimethoxy-6-methylnaphthyl | p-SO₃H-C₆H₄-CH₃ | 1.5 | 11 | powder | 53.53<br>53.29 | 5.88<br>5.97 | 8.61<br>8.69 | |
| 10 | −O−n−C₄H₉ | 3,2-diethoxy-6-methylnaphthyl | p-SO₃H-C₆H₄-CH₃ | 50 | 11 | 94−98 | 54.70<br>54.66 | 6.51<br>6.42 | 8.29<br>8.53 | |

TABLE 1-continued

| No. | R | R' | Addition Moiety | Concentration required to prolong the coagulation time by a factor of two (μM) | Preparation process (Ex. No.) | Property or m.p. (°C) | Elemental analysis Upper: Calculated Lower: Found C | H | N | I.R. (KBr) (cm⁻¹) |
|---|---|---|---|---|---|---|---|---|---|---|
| 11 | —O—CH₂CH₂OCH₃ | 3,7-di-OC₂H₅-naphthyl | SO₃H-p-tolyl·H₂O | 23< | 11 | 100–105 | 51.42 / 51.51 | 6.32 / 6.54 | 7.99 / 8.02 | |
| 12 | —O—CH₂CH=CHCH₃ | 3,7-di-OC₂H₅-naphthyl | SO₃H-p-tolyl | 4.5 | 11 | powder | 54.86 / 54.98 | 6.24 / 6.12 | 8.25 / 8.30 | |
| 13 | —O-n-C₄H₉ | 3-OCH₃, 1-OCH₃-7-methyl-naphthyl | SO₃H-p-tolyl | 5.5 | 11 | 148–151 | 53.36 / 53.50 | 6.18 / 6.20 | 8.59 / 8.60 | |
| 14 | 4-CH₃-piperidyl | 3,7-di-OCH₃-naphthyl | CH₃COOH | 0.15 | 4 | powder | 55.21 / 55.11 | 6.95 / 6.74 | 12.38 / 12.01 | 3,300 (broad) 1,635 |
| 15 | 4-C₂H₅-piperidyl | 3,7-di-OCH₃-naphthyl | CH₃COOH | 0.15 | 8 | powder | 55.01 / 54.93 | 7.28 / 7.14 | 12.34 / 12.28 | 3,380 3,180 1,635 |
| 16 | 4-C₂H₅-piperidyl | 3,7-di-OCH₃-naphthyl | HF | 0.15 | 1 | powder | 55.64 / 55.50 | 7.10 / 7.12 | 12.98 / 12.87 | |

TABLE 1-continued

| No. | R | R' | Addition Moiety | Concentration required to prolong the coagulation time by a factor of two (μM) | Preparation process (Ex. No.) | Property or m.p. (°C) | Elemental analysis Upper: Calculated Lower: Found C | H | N | I.R. (KBr) (cm⁻¹) |
|---|---|---|---|---|---|---|---|---|---|---|
| 17 | azepane (N-) | 6-methoxy-2-naphthyl with OCH₃ | CH₃COOH | 0.55 | 2 | powder | 55.21 / 55.04 | 6.95 / 6.78 | 12.38 / 12.26 | |
| 18 | morpholine (O, N-) | 6-methoxy-2-naphthyl with OCH₃ | CH₃COOH | 1.5 | 9 | powder | 52.07 / 51.88 | 6.37 / 6.26 | 12.65 / 12.26 | 3,360 3,180 1,640 |
| 19 | 4-methoxypiperidine | 6-methoxy-2-naphthyl with OCH₃ | CH₃COOH | 0.60 | 2 | powder | 53.69 / 53.48 | 6.72 / 6.68 | 12.04 / 12.00 | |
| 20 | 4-methylpiperazine | 6-methoxy-2-naphthyl with OCH₃ | 2CH₃COOH | 4.0 | 2 | powder | 51.75 / 51.49 | 6.76 / 6.39 | 13.41 / 13.21 | 3,400 3,200 1,640 |
| 21 | 4-methylpiperazine | 6-methoxy-2-naphthyl with OCH₃ | 2HF | 4.0 | 1 | powder | 50.54 / 50.48 | 6.64 / 6.21 | 15.37 / 15.28 | |
| 22 | 4-acetylpiperazine | 6-methoxy-2-naphthyl with OCH₃ | CH₃COOH | 1.5 | 3 | powder | 52.51 / 52.40 | 6.44 / 6.39 | 14.13 / 14.09 | |
| 23 | -N(H)(n-C₄H₉) | 6-methoxy-2-naphthyl with OCH₃ | CH₃COOH | | 3 | powder | 53.42 / 53.39 | 6.91 / 6.72 | 12.98 / 12.73 | 3,380 1,650 |

TABLE 1-continued $$\underset{H_2N}{\overset{HN}{>}}C-\underset{H}{\overset{H}{N}}-(CH_2)_3-\underset{\underset{R'}{|}}{\overset{}{CHCOR}}$$
$$HN-SO_2$$

| No. | R | R' | Addition Moiety | Concentration required to prolong the coagulation time by a factor of two (μM) | Preparation process (Ex. No.) | Property or m.p. (° C) | Elemental analysis Upper: Calculated Lower: Found | | | I.R. (KBr) (cm$^{-1}$) |
|---|---|---|---|---|---|---|---|---|---|---|
| | | | | | | | C | H | N | |
| 24 | $-\overset{H}{\underset{|}{N}}-CH_2CH_2OCH_3$ | 2,3-di-OCH$_3$ naphthyl | CH$_3$COOH | 0.5 | 5 | powder | 51.01 50.87 | 6.51 6.43 | 12.93 12.81 | 3,300 (broad) 1,640 |
| 25 | $-\overset{H}{\underset{|}{N}}-CH_2CH_2COOCH_3$ | 2,3-di-OCH$_3$ naphthyl | CH$_3$COOH | 7.0 | 5 | powder | 50.60 51.00 | 6.19 6.21 | 12.30 12.28 | 3,400 3,200 1,740 1,665 |
| 26 | $-\overset{H}{\underset{|}{N}}-CH_2CH_2COOC_2H_5$ | 2,3-di-OCH$_3$ naphthyl | CH$_3$COOH | 7.0 | 5 | powder | 51.45 51.37 | 6.39 6.26 | 12.00 11.69 | 3,200 (broad) 1,720 1,640 (broad) |
| 27 | 4-ethylpiperidinyl | 2,3-methylenedioxy naphthyl (dioxin-fused) | CH$_3$COOH | 10 | 3 | powder | 56.14 56.01 | 6.81 6.46 | 12.13 12.00 | 3,300 (broad) 1,635 |
| 28 | $-\overset{H}{\underset{|}{N}}-CH_2CH_2COOCH_3$ | 2,3-di-OC$_2$H$_5$ naphthyl | CH$_3$COCH | 7.0 | 3 | powder | 52.25 52.21 | 6.58 6.48 | 11.72 11.56 | |
| 29 | $-\overset{H}{\underset{|}{N}}-CH_2CH_2COOC_2H_5$ | 2,3-di-OC$_2$H$_5$ naphthyl | CH$_3$COCH | 7.0 | 3 | powder | 53.02 52.67 | 6.76 6.41 | 11.45 11.04 | |
| 30 | $-\overset{CH_3}{\underset{|}{N}}-n-C_4H_9$ | 2,3-di-OC$_2$H$_5$ naphthyl | CH$_3$COOH | 30 | 3 | powder | 55.75 55.81 | 7.45 7.22 | 12.04 12.34 | 3,360 1,630 1,260 1,140 |

TABLE 1-continued $$\begin{array}{c} HN \\ \phantom{HN}\diagdown \\ \phantom{HN}C-N-(CH_2)_3-CHCOR \\ H_2N \phantom{ii} H \phantom{iiiiiiiiii} | \\ \phantom{H_2Niiiiiiiiiiiii} HN-SO_2 \\ \phantom{H_2Niiiiiiiiiiiiiiiiiiii} | \\ \phantom{H_2Niiiiiiiiiiiiiiiiiiii} R' \end{array}$$

| No. | R | R' | Addition Moiety | Concentration required to prolong the coagulation time by a factor of two (μM) | Preparation process (Ex. No.) | Property or m.p. (°C) | Elemental analysis Upper: Calculated Lower: Found | | | I.R. (KBr) (cm$^{-1}$) |
|---|---|---|---|---|---|---|---|---|---|---|
| | | | | | | | C | H | N | |
| 31 |  | 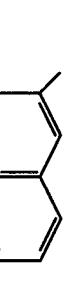 | CH$_3$COOH | 8.5 | 3 | powder | 56.64 56.51 | 7.70 7.65 | 11.80 11.98 | 3,350 1,640 1,260 1,160 |
| 32 | 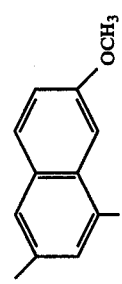 |  | CH$_3$COOH | 0.075 | 3 | powder | 55.21 54.93 | 6.95 6.73 | 12.38 12.15 | |
| 33 |  |  | CH$_3$COOH | 0.10 | 3 | powder | 55.01 54.84 | 7.28 7.16 | 12.34 12.03 | |
| 34 |  |  | CH$_3$COOH | 5.5 | 3 | powder | 57.31 57.55 | 7.46 7.71 | 11.52 11.32 | 3,350 1,680 1,160 |
| 35 |  |  | CH$_3$COOH | 0.8 | 3 | powder | 56.73 56.75 | 5.82 5.71 | 12.25 11.98 | 3,350 1,650 1,150 |
| 36 |  | 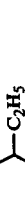 | HF | 15 | 12 | powder | 54.41 54.70 | 7.47 7.45 | 14.42 14.31 | 3,300 (broad) 1,640 |
| 37 |  |  | CH$_3$COOH | 25 | 13 | powder | 52.35 52.65 | 7.07 7.01 | 13.27 13.12 | 3,320 1,640 |

TABLE 1-continued $$\begin{array}{c} HN \\ \diagdown \\ C-N-(CH_2)_3-CHCOR \\ / \quad | \quad | \\ H_2N \quad H \quad HN-SO_2 \\ \quad\quad\quad\quad | \\ \quad\quad\quad\quad R' \end{array}$$

| No. | R | R' | Addition Moiety | Concentration required to prolong the coagulation time by a factor of two (μM) | Preparation process (Ex. No.) | Property or m.p. (°C) | Elemental analysis Upper: Calculated Lower: Found | | | I.R. (KBr) (cm⁻¹) |
|---|---|---|---|---|---|---|---|---|---|---|
| | | | | | | | C | H | N | |
| 38 | 4-C₂H₅-piperidine | methyl-benzodioxepine | CH₃COOH | 5 | 14 | powder | 53.22 / 53.31 | 7.26 / 7.04 | 12.93 / 12.87 | 3,350 (broad) 1,635 |
| 39 | 4-CH₃-piperidine | methyl-benzodioxepine | CH₃COOH | 8 | 13 | powder | 52.35 / 52.60 | 7.07 / 6.93 | 13.27 / 13.40 | 3,100 (broad) 1,640 |
| 40 | morpholine | methyl-benzodioxepine | CH₃COOH | 25 | 14 | powder | 48.92 / 49.21 | 6.45 / 6.45 | 13.58 / 13.41 | 3,400 3,120 1,640 |
| 41 | N(CH₃)(C₄H₉) | methyl-benzodioxepine | CH₃COOH | 100 | 13 | powder | 51.25 / 51.53 | 7.23 / 7.46 | 13.58 / 13.29 | 3,350 1,640 1,280 |
| 42 | 4-C₂H₅-piperidine | methoxy-benzodioxepine | — | 6 | 13 | powder | 53.99 / 53.75 | 7.29 / 7.61 | 13.69 / 13.50 | 3,400 1,630 |
| 43 | 4-C₂H₅-piperidine | methyl-dibenzofuran | CH₃COOH | 0.3 | 13 | powder | 58.62 / 58.32 | 6.85 / 6.58 | 12.21 / 11.99 | 3,340 1,630 1,265 |
| 44 | 4-C₂H₅-piperidine | methyl-dibenzofuran | ½H₂O | 0.3 | 13 | powder | 59.03 / 58.84 | 6.54 / 6.48 | 13.77 / 13.63 | 3,350 1,630 1,275 |
| 45 | 4-C₂H₅-piperidine | methyl-dibenzofuran | CH₃COOH | 0.2 | 13 | powder | 57.94 / 57.64 | 6.66 / 6.65 | 12.51 / 12.24 | 3,350 1,630 1,160 |
| 46 | 4-C₂H₅-piperidine | methyl-dibenzodioxine | CH₃COOH | 0.15 | 13 | powder | 56.33 / 56.08 | 6.48 / 6.45 | 12.17 / 11.96 | 3,300 1,630 1,290 |

TABLE 1-continued

Structure:
$$H_2N-C(=NH)-NH-(CH_2)_3-CH(NH-SO_2-R')-COR$$

| No. | R | R' | Addition Moiety | Concentration required to prolong the coagulation time by a factor of two (μM) | Preparation process (Ex. No.) | Property or m.p. (°C) | Elemental analysis Upper: Calculated Lower: Found | | | I.R. (KBr) (cm$^{-1}$) |
|---|---|---|---|---|---|---|---|---|---|---|
| | | | | | | | C | H | N | |
| 47 | (azepane ring with CH$_3$, N-linked) | (dibenzofuran with methyl) | CH$_3$COOH | 0.5 | 13 | powder | 57.23 | 6.47 | 12.84 | 3,350 |
| | | | | | | | 57.01 | 6.41 | 12.61 | 1,635 1,270 |
| 48 | (N-C$_4$H$_9$, N-CH$_3$) | (xanthene-type with methyl) | CH$_3$COOH | 5 | 13 | powder | 57.02 | 6.81 | 12.79 | 3,310 |
| | | | | | | | 56.74 | 6.93 | 12.65 | 1,640 1,260 |

What is claimed as new and intended to be covered by letters patent is:

1. An $N^2$-substituted-L-argininamide having the formula:

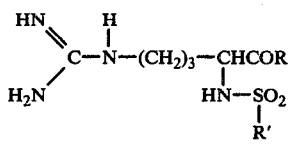

and the pharmaceutically acceptable acid addition salts thereof, wherein R is

wherein Z is a divalent group which consists of at least two groups selected from methylene —$CH_2$— and monosubstituted methylene

wherein $R_4$ is selected from the group consisting of $C_1$–$C_{10}$ alkyl and $C_1$–$C_{10}$ alkoxy, and at least one group selected from the group consisting of oxy —O—, thio —S—, alkyl substituted imino

wherein $R_5$ is $C_1$–$C_{10}$ alkyl, and acyl substituted imino

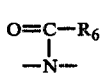

wherein $R_6$ is $C_1$–$C_{10}$ alkyl, which are combined in an arbitrary order, the number of the combined groups being up to 20; and R' is selected from the group consisting of

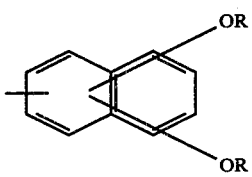

wherein R" and R'" when considered separately are $C_1$–$C_{10}$ alkyl, or R" and R'" when taken together are $C_1$–$C_{10}$ alkylene;

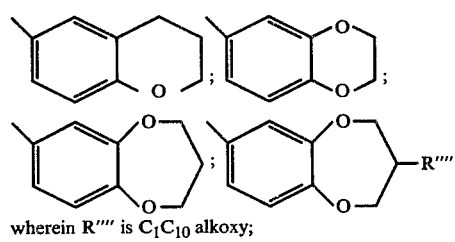

wherein R"" is $C_1C_{10}$ alkoxy;

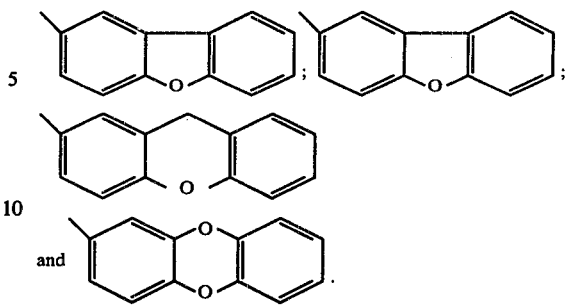

and

2. The compounds of claim 1, wherein R is selected from the group consisting of tetrahydro-1, n-oxazin-n-yl, wherein n is an integer of 2, 3 or 4; tetrahydro-1, n-thiazin-n-yl, wherein n is an integer of 2, 3 or 4; 1-piperazinyl substituted with a group selected from $C_1$–$C_5$ alkyl and $C_1$–$C_5$ acyl; and R' is selected from the group consisting of

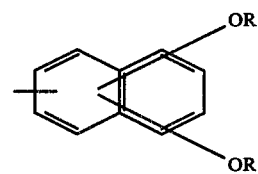

wherein R" and R'" when considered separately are $C_1$–$C_5$ alkyl, or R" and R'" when taken together are $C_1$–$C_5$ alkylene;

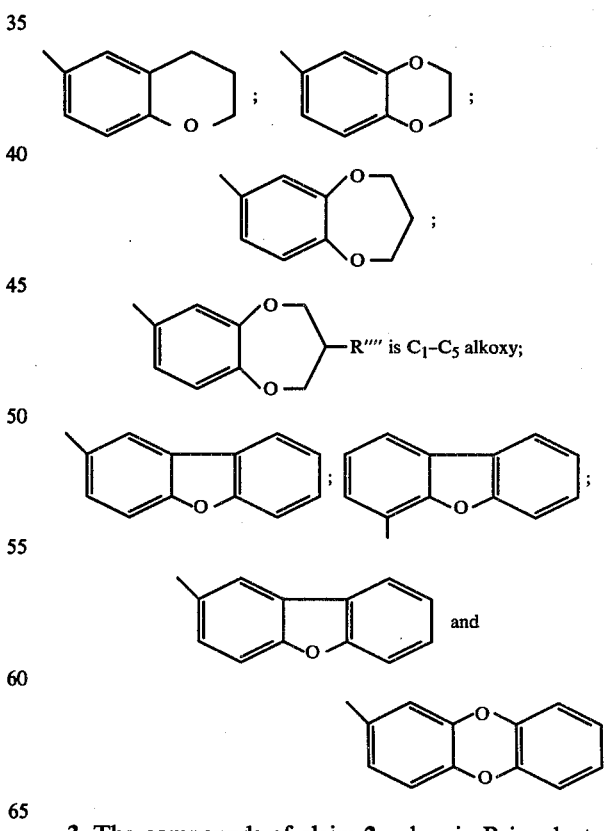

3. The compounds of claim 2, wherein R is selected from the group consisting of, morpholine, tetrahydro-1,4-thiazin-4-yl, 4-methyl-1-piperazinyl and 4-acetyl-1- piperazinyl; and R' is selected from the group consisting of

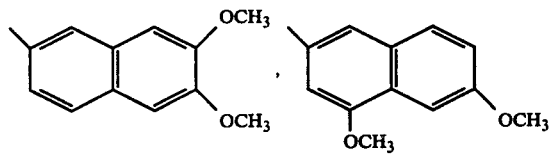

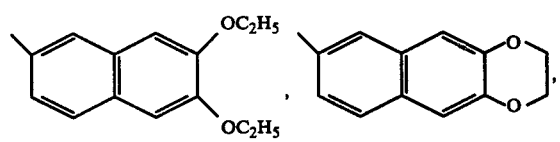

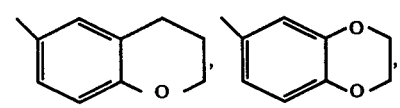

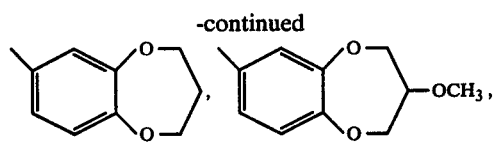

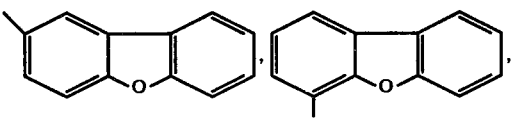

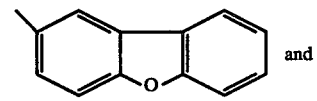 and

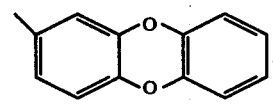

4. The compound of claim 1 which is 4-[$N^2$-(6,7-dimethoxy-2-naphthalenesulfonyl)-L-arginyl] morpholine.

5. A pharmaceutical composition which comprises an amount of a compound of cliam 1, effective for inhibiting activity and suppressing activation of thrombin in vivo, and a pharmaceutically acceptable carrier.

* * * * *